(12) United States Patent
Prat Bartomeu (10) Patent No.: US 7,931,370 B2
(45) Date of Patent: Apr. 26, 2011

(54) EYE MOVEMENT SENSOR DEVICE (75) Inventor: Joan Prat Bartomeu, Barcelona (ES)

(73) Assignee: Hospital Sant Joan de Deu, Barcelona (ES)

( * ) Notice: Subject to any disclaimer, the term of this patent is extended or adjusted under 35 U.S.C. 154(b) by 439 days.

(21) Appl. No.: 11/916,156

(22) PCT Filed: Jun. 2, 2006

(86) PCT No.: PCT/ES2006/000325
§ 371 (c)(1), (2), (4) Date: Nov. 30, 2007

(87) PCT Pub. No.: WO2006/128939
PCT Pub. Date: Dec. 7, 2006

(65) Prior Publication Data
US 2008/0192204 A1 Aug. 14, 2008

(30) Foreign Application Priority Data
Jun. 3, 2005 (ES) .................................. 200501342

(51) Int. Cl.
*A61B 3/00* (2006.01)
*A61B 3/14* (2006.01)
(52) U.S. Cl. ........................................ 351/209; 351/200
(58) Field of Classification Search .................. 351/200, 351/206, 208, 209, 211, 205
See application file for complete search history.

(56) References Cited

U.S. PATENT DOCUMENTS

| | | | |
|---|---|---|---|
| 4,852,988 A * | 8/1989 | Velez et al. .................... 351/210 |
| 5,070,883 A | 12/1991 | Kasahara | |
| 5,094,521 A | 3/1992 | Jolson et al. | |
| 5,550,601 A | 8/1996 | Donaldson | |
| 5,776,068 A | 7/1998 | Silverman et al. | |
| 2003/0086061 A1 | 5/2003 | Pfleger | |
| 2005/0174535 A1* | 8/2005 | Lai et al. ........................ 351/205 |
| 2006/0025685 A1* | 2/2006 | dela Houssaye .............. 600/443 |
| 2006/0098087 A1* | 5/2006 | Brandt et al. ................... 348/61 |

FOREIGN PATENT DOCUMENTS

| | | |
|---|---|---|
| EP | 0940117 | 9/1999 |
| WO | 9319661 | 10/1993 |
| WO | 03/068059 | 8/2003 |
| WO | 2004041078 A2 | 5/2004 |

OTHER PUBLICATIONS

International Search Report dated Nov. 17, 2006 from the corresponding PCT/ES2006/000325.
International Preliminary Report on Patentability dated Sep. 7, 2007 from the corresponding PCT/ES2006/000325.

* cited by examiner

*Primary Examiner* — Ricky L Mack
*Assistant Examiner* — Brandi N Thomas
(74) *Attorney, Agent, or Firm* — Katten Muchin Rosenman LLP (57) ABSTRACT

The eye movement sensor comprises a helmet (1) adjustable to the head of a patient who is undergoing an ophthalmologic examination, in a unit with seat (10) and projection screen (11) of light spots in front, the same helmet (1) incorporating a front light projector (2) which emits a light spot towards the screen (11), as well as means of image recording of each one of the eyes, which records their movements captured from an angle which permits viewing the eye in all its positions. Said means of recording preferably consists of a video camera (6) disposed below the projector (2) of the helmet (1), focussing a pair of mirrors (7), incorporated on different sides of the lower part of the helmet (1) downward, under each eye respectively, to capture the specular reflection of its movements; or instead, two cameras (5) under each eye.

19 Claims, 6 Drawing Sheets

EYE MOVEMENT SENSOR DEVICE

OBJECT OF THE INVENTION

The present invention is applied to the field of ophthalmology, in particular for the detection, monitoring and optimization of the further treatment of pathologies related to certain ocular motility anomalies, such as those caused by facial paralysis, strabismus (eye deviation), blepharospasm (spastic closure of the eyes), nystagmus (accelerated eye vibration), ptosis (drooping upper eyelid), as well as the examination of eye prosthesis, etc.

In particular, the eye movement sensor recommended comprises a helmet, applicable to both adult and children patients, which incorporates means of recording the eyes, preferably a video camera for both eyes or one for each eye, which record them in images viewed from an angle which permits capturing all their movements, which is the angle of the gaze in maximum infraduction, i.e. downward. Additionally, the helmet has a light projector which emits light spots towards a screen, which the patient is made to look at to undergo a very precise eye examination of said anomalies and optimize the diagnosis.

The object of the invention is for the patient to be able to freely move his/her head when looking at the visual tests that are normally undergone during an ophthalmologic examination, permitting a more pleasant and shorter examination, whose results are not affected by said voluntary or involuntary head movements.

Likewise, an object of the invention is to collect the eye movements in any of their possible positions, recording them in images by the means of recording incorporated in the helmet, for their subsequent processing and analysis by means of appropriate computer equipment.

BACKGROUND OF THE INVENTION

Normally, when a person fixes their attention on an object and follows it with his/her gaze, both eyes move in unison keeping them focussed on the same point. But, if certain pathologies are present in the subject, this does not happen and some people, largely children, suffer a deviation of one eye with respect to another, so that whilst one eye remains fixed looking at a point (fixating eye), the other does not do so, instead it remains in a deviated position (deviated or strabismic eye). This ophthalmologic disease is often known with the name of strabismus.

There are many ways of dividing the classes of strabismus; one of the most important is that it depends on the variability of the eye deviation:
  Concomitant: the deviation of the eyes does not vary or varies little in the different gaze positions. This is the most frequent strabismus in a child.
  Incomitant: the deviation of the eyes varies according to the gaze positions or is only manifested in some of them. This group includes the strabismus produced by paralysis of the nerves which are directed towards the muscles or by lesions of the muscles (degeneration or citatrization).

Furthermore, depending on the direction of the eye deviation, strabismus can be classified as:
  Esotropia (inward)
  Exotropia (outward)
  Hypertropia (upward)
  Hypotropia (downward)
  Cyclotropia (inward or outward rotation)

From an epidemiological perspective, although strabismus was a pathology that saw its frequency in developed countries decrease from the decade of the seventies until the end of the century, due to the narrowing in the population base, this trend has reversed in recent years due to different factors present in current society:
  1. The new increase in birth rate
  2. Greater susceptibility of suffering the disease in new rising population groups: immigrants, adopted children from less developed countries and premature babies with the increase in assisted fertilization techniques (in vitro, etc.).

Therefore, it is estimated that the incidence of strabismus in developed countries is approximately 4%, which means an increase in children undergoing said ophthalmologic diagnosis and treated for this type of pathology could be expected during one or two decades.

Specifically, in the province of Barcelona around 5000 ocular motility examinations are carried out on children annually, also exceeding one thousand examinations in adults, which gives rise to a high number of strabismus surgical procedures and more particularly, in the Hospital Sant Joan of Déu, around 500 children are operated on for strabismus per year.

Taking the overall statistics into consideration, the need arises for a constant adaptation of ophthalmologic medicine to the populations' changing health requirements, placing emphasis on the first phases of the disease and the prevention with diagnostic systems better adapted to patients and which cover the greatest possible number of pathologies in its detection functionality, which can be extended to the collaboration in treatment and monitoring of eye disease.

To date, a multitude of systems are known which permit determining and measuring possible ocular mobility alterations, but they all have one or several of the following problems
  Active collaboration is required from the patient, which is difficult to achieve for children under the age of 6 and especially in mentally handicapped patients.
  The lack of precision in measuring the ocular parameters leads to the excessively subjective interpretation of the results obtained with most of the existing diagnosis systems.
  The strabismus detecting means known do not permit measuring deviation of the eyes at all points in the field of ocular motility of a person.

In this regard, we can quote International Patent application PCT WO 93/19661 which provides an apparatus for testing ocular motility, which incorporates a light projector controlled by a computer and a screen where a light spot is projected, which the subject undergoing said eye examination should follow with his/her gaze. Therefore, the patient should be sitting down staring at the screen, if he/she is a child, there is usually little collaboration and means of fixing the child's head or controlling his/her movements needs to be included in the system to be able to obtain valid eye motility tests with the method set down in WO 93/19661. Furthermore, this method and the apparatus that executes it are based on the use of a pair of video cameras disposed frontally, in the visual axis of each eye respectively, but their position does not permit recording their entire visual field, and, in particular, prevents recording a downward gaze, since the upper lid covers the eye. Another deficiency is that the video cameras are fixed only recording the eyes, but means for capturing movements of the head are not provided, which means the ocular motility detected with this method and apparatus is not correct if the patient, as is typical in children or the mentally handicapped, moves his/her head.

Another example of apparatus to evaluate the alignment of the eyes is that disclosed in U.S. Pat. No. 5,094,521, which involves a drastic solution to the problem posed if the patient makes voluntary or involuntary head movements, avoiding this by immobilizing the head with tapes which are fixed to a support wherein the person should place his/her face, with the chin resting on a chinrest, so that the eyes remain perfectly aligned, through which he/she is made to look at a screen with light spots. Evidently, its seems very improbable that a young person or people with mental problems would tolerate the rigid fixing of his/her head, which in any case is uncomfortable even simply using velcro tapes. Furthermore, the fixed screen, which is positioned in front of the subject and has multiple light spots, incorporates a video camera in the centre to record both eyes at the same time. Nor can the camera, therefore, as in the previous apparatus, of document WO 93/19661, capture the movement of the eyes when the patient looks down, being very sensitive to small head movements which, even with the fixing tapes, the person makes on rotating the eyes in a sideward gaze, which falsifies the evaluation of ocular deviation.

An alternative which resolves the possible head movements, voluntary or involuntary, connected to eye movement, is the unit disclosed in European Patent EP 0940117, where the patient is free to move his/head, since it has means of control which detects its position, calculating the coordinates on the three axes (x, and, z) of the head by infrared. Infrared is also used to measure ocular motility, having an infrared detector for each eye, but these detectors do not move together with the head, but the captured measurements of the eye movements are independent from those taken concerning whether the patient moves his/her head. Children or even adults with any mental or physical disorders which causes chaotic movements of the head may cause too large movements of their head position, it being practically impossible to make reliable calculations of the eye movements, with respect to the point at which the gaze is directed, as it is easily possible to go outside the capturing area marked by the infrared detecting means. For these and other motives, such as the fact that the patient should be in continuous communication with the examiner by means of a helmet with microphone and headphones, the functioning of this system entails its exclusive application to very collaborative adults for it to be really effective, at least in the conceptual aspect.

DESCRIPTION OF THE INVENTION

The present invention resolves, among others, the aforementioned problems, in a fully satisfactorily manner in each and every one of the different aspects commented, offering interesting advantages compared with the references.

In particular, the invention described is devised to capture eye movements, in view of its application in the detection of anomalies derived from strabismus or other diseases of the eyes and eyelids, in all types of patients, from adults in full possession of their mental and physical faculties to children under the age of six who do not provide sufficient collaboration in an ophthalmologic examination.

The eye movement sensor which is recommended comprises a helmet, in short a device designed ergonomically for the head, which incorporates means of recording of the eyes, which basically consists of at least one camera, preferably a video, to record images of each one of the eyes.

In this way, since the means of capturing eye movements, i.e. the cameras that record the eyes, are associated in fixed manner by the helmet which the subject being ophthalmologically examined has to put on; although he/she moves his/her head, the movements of the eyes continue to be recorded without decentering the stills, irrespective of these involuntary head movements that normally occur.

Depending on the patient's age, the ergonomic eye movement sensor is designed according to different variants:

For adults, the helmet has two cameras positioned at the height of the cheeks being able to record the mobility of each eye separately and both simultaneously.

For a child patient, the helmet is equipped with a single camera at the front, with the camera lens directed downward, which captures the eye movements reflected by means of different mirrors close to the eyes, provided in the same helmet; thus, its movements are reflected in a tiny mirror for each eye and are recorded by a single central camera.

This second alternative of embodiment of the invention is also applicable for ocular examination in adults.

To adapt the device to the size of the head, another helmet of smaller size is provided, which, in turn, is attached to the main helmet that incorporates the camera, the smaller one normally fitting inside the first, which is made with the dimensions corresponding a large diameter adult cranium.

The helmet construction may be of comprehensive type, which is fitted directly to the head, or have conventional means of fixing, such as an elastic tape, tapes with velcro or other known fastening or an adjustable arc of the type with which the indirect ophthalmoscopes are currently supported on the ophthalmologist's head. Preferably the rear third of the helmet is left open so that when the patient is sitting for a more comfortable examination, the support of the head on the back of a seat does not affect the helmet's position with respect to the head.

To record eye movements, there is only one angle of observation which allows the eye to be seen in any of its rotation positions. Said angles correspond to the direction of the gaze in maximum infraduction, i.e. downward. This means that the camera or the two cameras used in the possible embodiments of the device, positioned in the described form, have the capacity to record the eyes, moving in a coronal plane, at 270° (6 h), the patient's face looking ahead, as well as in the sagital plane, at approximately 240°, looking from the right profile of the patient.

The cameras incorporated in the helmet are high resolution and with the possibility of capturing images with high colour discrimination, in the precise light conditions required for the ophthalmologic examination, in order to subsequently permit digital processing of said images in a computer system to which the recordings may be transmitted.

Optionally, the helmet of the eye movement sensor has a support for corrective lenses, when the patient needs them due to his/her visual deficiency, so that said support with the optical correction lenses does not hamper the recording carried out by the helmet cameras.

The helmet of the invention, designed to be used as an integral part of a unit for ophthalmologic examination, will incorporate in its upper part a light projector, preferably a laser emitter, whereby the projector of the light spot at which the patient is made to look during the examination is displaced in unison with the head if the patient moves it.

In this way, the eye recording cameras and the projector of the objective light spot on which is gaze is fixed incorporated in the same device, which is the helmet, attached to the subject's head, manage to avoid the problem of involuntary movements of the head on rotating the eyes towards the objective point. Here, both the projector and the cameras capturing the eye movements are jointly displaced with the head, minimizing the misalignments that may arise from taking the images that should be processed in a later phase by a computer whereto the recorded images are transferred.

Integrated in an ophthalmologic unit, which usually comprises at least one seat, so that the patient takes the examination sitting down, and a screen where the objective light spot is projected, the device disclosed has important improvements with respect to the references seen.

With respect to the two first documents quoted in the references, WO 93/19661 and U.S. Pat. No. 5,094,521, the main advantage of the device of the invention is that the patient is free to move his/her head, within the reasonable limits set by the situation in which the person sat down to be examined is in, whilst in the documents mentioned, it is essential for the head to be still so that the measurements resulting from the examination are reliable and, specifically, the apparatus of U.S. Pat. No. 5,094,521 specifies the use of tapes to force the head to be in a fixed position, which makes these apparatus of the state of the art technically unsuitable, especially for use with child patients.

On the other hand, although documents WO 93/19661 and U.S. Pat. No. 5,094,521 speak of the use of video cameras to record the patient's eyes, its fixed location on the subject's forehead does not allow them to be captured when he/she looks down, whilst the eye movement capturing means incorporated in the helmet, as is proposed in the device of the invention, in the positions that have been previously described, with the cameras under the eyes or the central camera focussing towards the mirrors provided in the helmet under the eyes recording their reflection, can always capture a downward gaze and, in short, they are capable of viewing both eyes in all their positions.

With regard to the last document mentioned in the references, EP 0940117, the improvement of the invention, which is also observed on comparing it with the other documents, stems from the fact that the eye movement sensors or the set of camera plus mirrors integrated in the helmet, move with the head. Nevertheless, in EP 0940117, where it also speaks of a helmet and infrared movement sensors, both of the eyes and of the head which is not forced in a fixed position, said eye movement sensors are separated from the helmet, which means that when the head moves chaotically in the space, the calculation of the eye movements with the other infrared sensors outside the helmet would lack reliability.

Additionally, in the embodiment of the invention, wherein the device incorporates a light projector in the helmet with the means of eye movement capturing or recording, the tests with light spots which are made in the ophthalmologic examination are also connected to head movement. In contrast, in the references seen these tests with light spots are projected in a manner unconnected to any possibility of the patients moving his/her head, nullifying the reference measures of the position of the gaze and the persons objective point.

In addition to the detection, measuring and monitoring of strabismus, the invention has other uses in ophthalmology, such as other eye diseases which can be evaluated by capturing images of the eye movements for later computer analysis which may appear in a still of an eye. For example:

Determination of the rotation angles of an ocular prosthesis.
Analysis of the dynamics of the upper eyelid in ptosis (drooping of the upper eyelid).
Evaluation of the defect of voluntary and involuntary eye closure in facial paralysis (impossibility of closing the eye).
Capturing blepharospasm (spastic closure of the eyes)
Study of nystagmus, which is a high-speed involuntary eye vibration, with cameras in the helmet capable of recording more than 25 stills persecond.

DESCRIPTION OF THE DRAWINGS

To complement the description being made and with the object of helping towards a better understanding of the characteristics of the invention, in accordance with a preferred example of practical embodiment thereof, a set of figures is attached as an integral part of the description, wherein the following has been represented with an illustrative non-limitative character.

PREFERRED EMBODIMENT OF THE INVENTION

Figure 1:
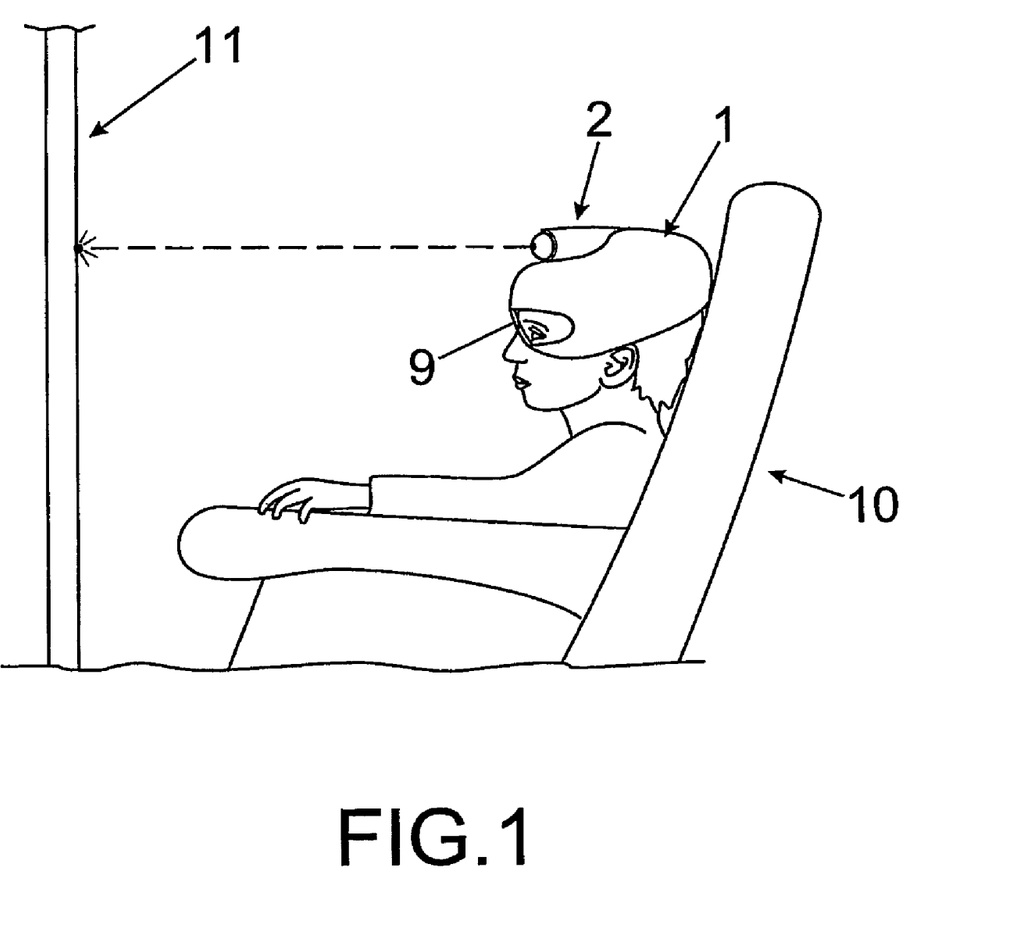
FIG. 1 Shows a schematic representation of the unit for ophthalmologic examinations where the eye movement sensor of the invention is applied, illustrating the helmet the device comprises, according to a preferred embodiment, placed on the patient's head.

As represented in FIG. 1, the eye movement sensor comprises a helmet (1) which is fitted to the head of a subject who is undergoing an ophthalmologic examination in a unit, where the subject sits comfortably in a seat (10) and in front of which there is a light spot projection screen (11), situated at the appropriate distance for the examination, having oriented the seat (10) conveniently to place the subject in the position required for a correct examination.

To project the light spots at which the examiner duly makes the subject look, the helmet (1) incorporates a light projector (2), located in its upper, front and central part, which emits a light spot towards the projection screen (11).

Figure 2:
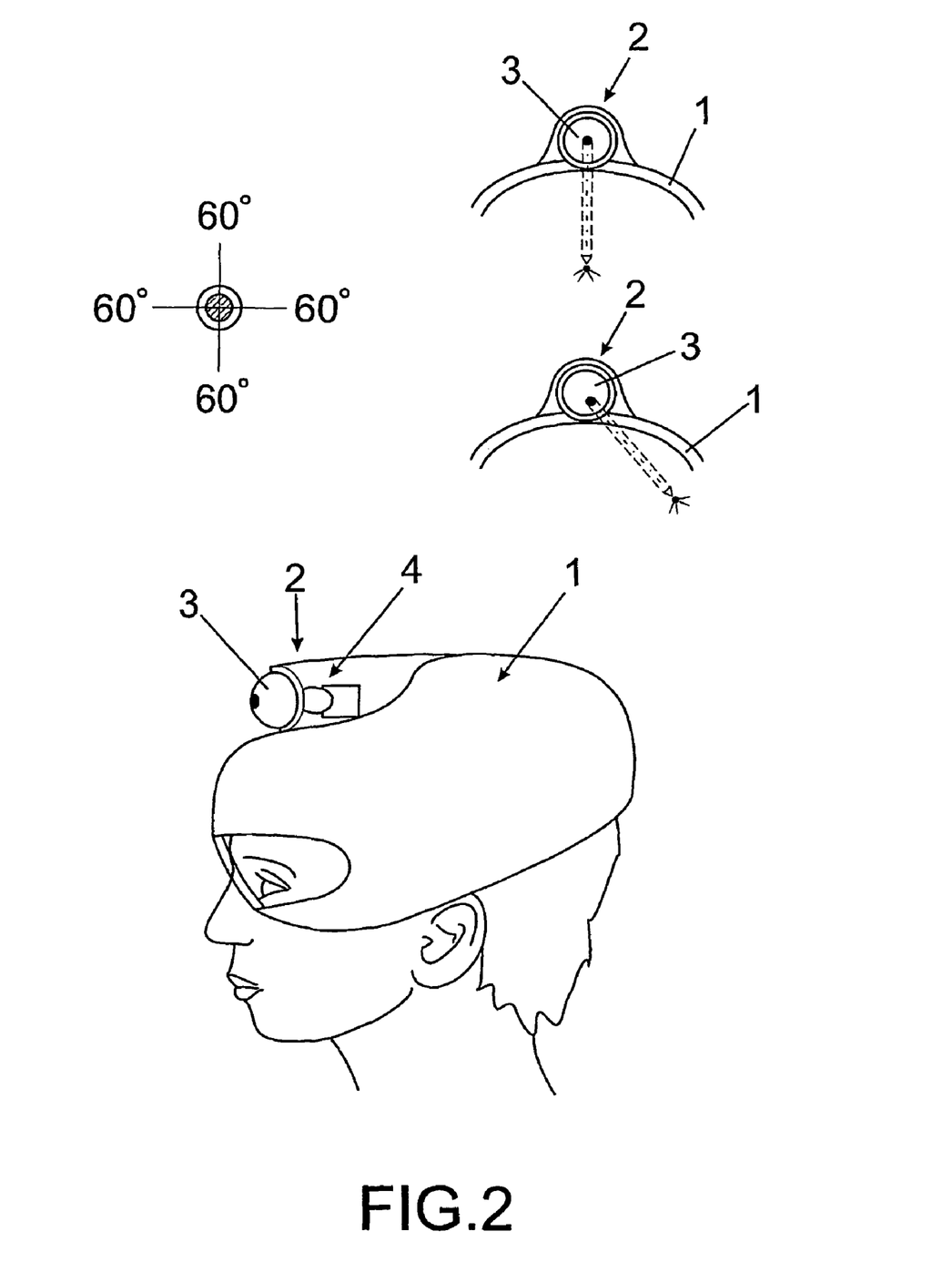
FIG. 2 Shows schematic detailed representations of the laser light projector incorporated in the helmet in a preferred embodiment.

As illustrated in FIG. 2, a preferred embodiment can be described which consists of incorporating a light projector (2) in the helmet (1), which emits a laser beam, so that it is projected on the projection screen (11) as a circular image or a light spot. Said laser light projector (2) comprises a rotatory sphere with a laser pointer (3) which shoots the beam over the surface of the sphere forward in a specific direction, upward, downward, right and left, covering angles of up to 60° in the rotation of the sphere with the pointer (3), which is achieved by the action of an electric motor (4), incorporated in the helmet (1).

Figure 3:
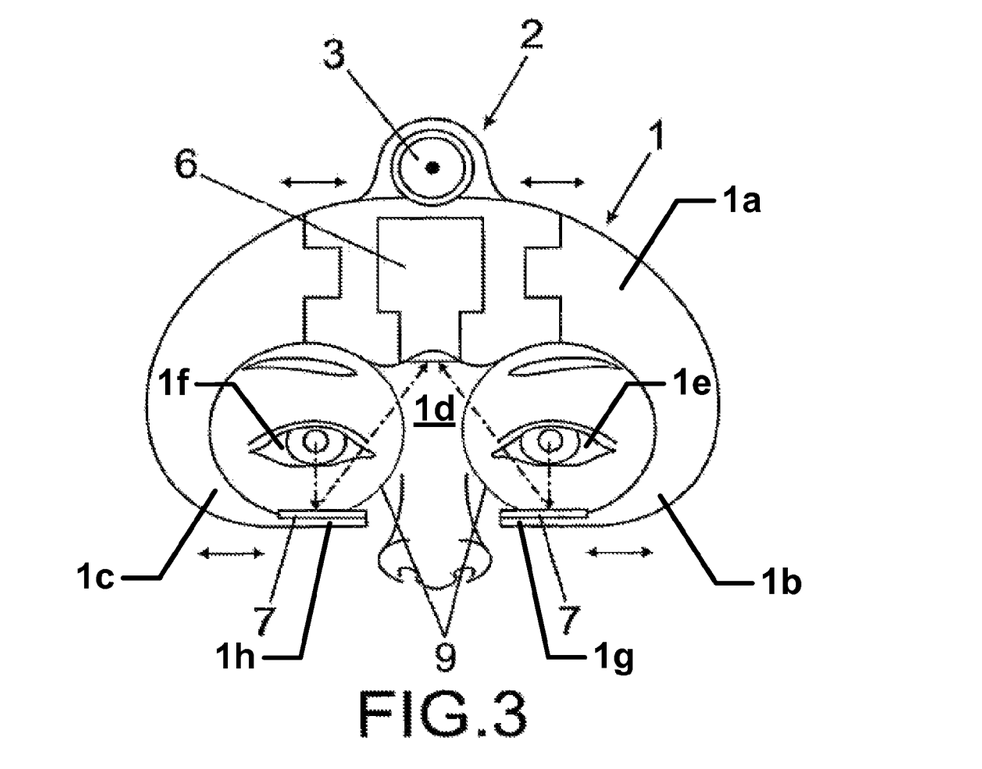
FIG. 3 Shows a front view of the helmet which incorporates a video camera below the light projector and two mirrors under the eyes to reflect the eye movements which are recorded by said camera, in accordance with the object of the invention.

Below the light projector (2), as shown in FIG. 3, in the upper and central part of the helmet (1), at the height of the subject's forehead, said helmet (1) incorporates a video camera (6) which focuses its lens downward, having provided, in the lower part of the helmet (1), a pair of mirrors (7), under each eye respectively on one side of the helmet (1), where the different eye movements are reflected which are recorded by the video camera (6). This configuration enables the recording of all the possible positions of the eyes as the patient moves them following the light spot produced by the light projector (2), on capturing the eyes seen from below, at an angle of approximately 45° to 50°, reflected in the respective mirrors (7), as shown in FIG. 4.

Figure 4:
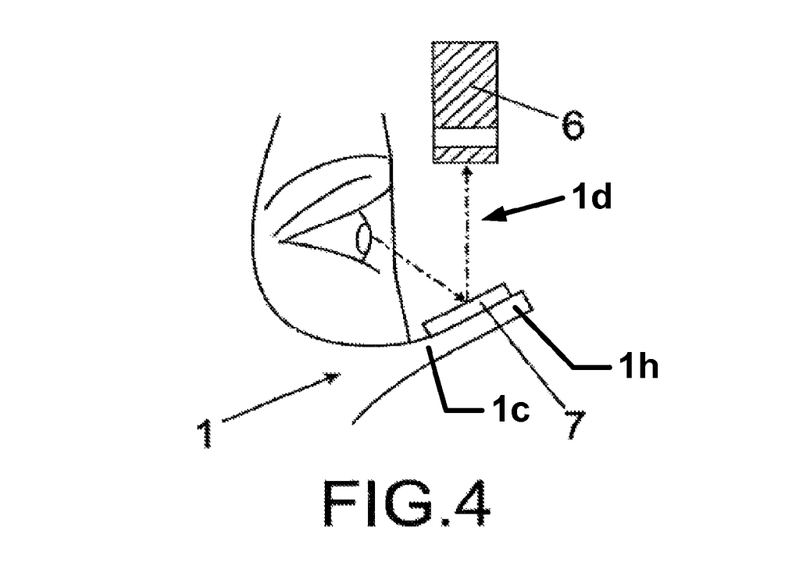
FIG. 4 Shows a detailed side view of the helmet camera and one of the mirrors under the eye, in accordance with the embodiment of the helmet illustrated in the previous figure.

As illustrated in FIGS. 3 and 4, helmet (1) includes a head covering portion (1a) and a pair of cheek-extending portions (1b and 1c) defining a central open area (1d) for leaving eyes of the patient (1e and 1f) unobstructed by the helmet (1). When the helmet is worn by the patient, each cheek-extending portion (1b and 1c) extends from proximal to an ear of the patient (FIG. 1) over a cheek portion of the patient (FIG. 1) and has a distal end (1g, 1h) proximate to a respective front face portion under the respective eye of the patient.

Figure 5:
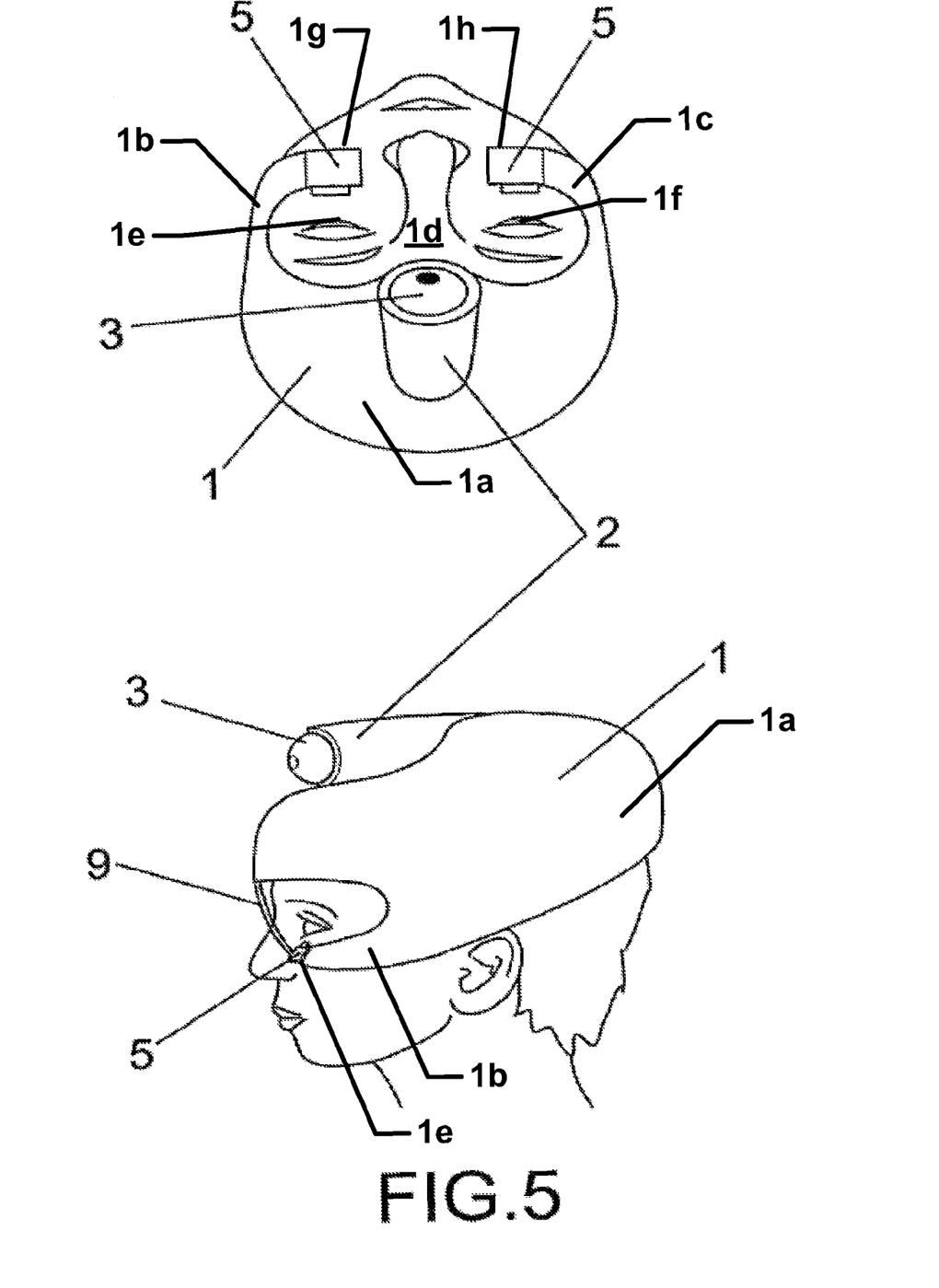
FIG. 5 Shows a top view and another side view of the helmet according to another possible embodiment, wherein it has two video cameras, one under each eye to record their respective movements, in accordance with the object of the invention.

Another alternative embodiment is that represented in FIG. 5, where the helmet (1) has two video cameras (5), instead of one, disposed respectively (1) under the eyes, at the height of the subject's cheeks, instead of being positioned on the forehead as in the previous embodiment of the helmet (1). In this configuration, the indirect recording by means of specular reflections, as in the embodiment of the aforementioned invention, is not necessary but instead the video cameras (5) directly capture all the eye movements as they are located under each one thereof.

As illustrated in FIG. 5 helmet (1) includes a head covering portion (1a) and a pair of cheek-extending portions (1b and 1c) defining a central open area (1d) for leaving eyes of the patient (1e and 1f) unobstructed by the helmet (1). When the helmet is worn by the patient, each cheek-extending portion (1b and 1c) extends from proximal to an ear of the patient (FIG. 1) over a cheek portion of the patient (FIG. 1) and has a distal end (1g, 1h) proximate to a respective front face portion under the respective eye of the patient.

In any case, the video cameras (5, 6) are light, around a weight of 60-90 grams, with high resolution, since at least between 200 and 400 pixels resolution is required to capture all the positions of one extreme to the other of an eye, considering its angle of maximum movement, which is around 100°.

Figure 6:
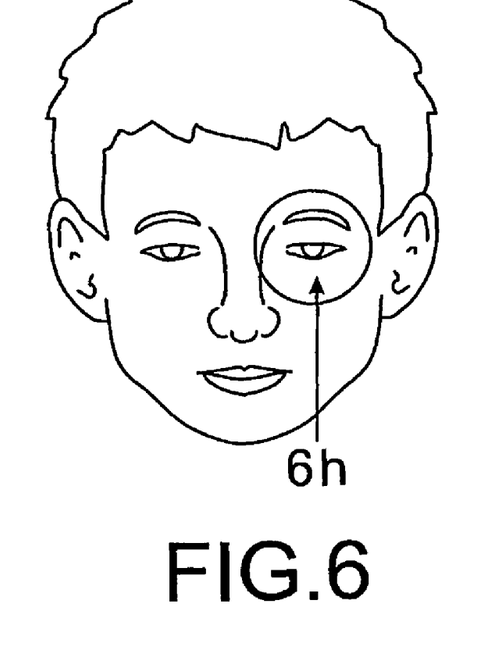
FIG. 6 Shows a front view of the patient's face, where it indicates the situation of a coronal plane, where the eye movement capturing means are positioned, seen from the front.
Figure 7:
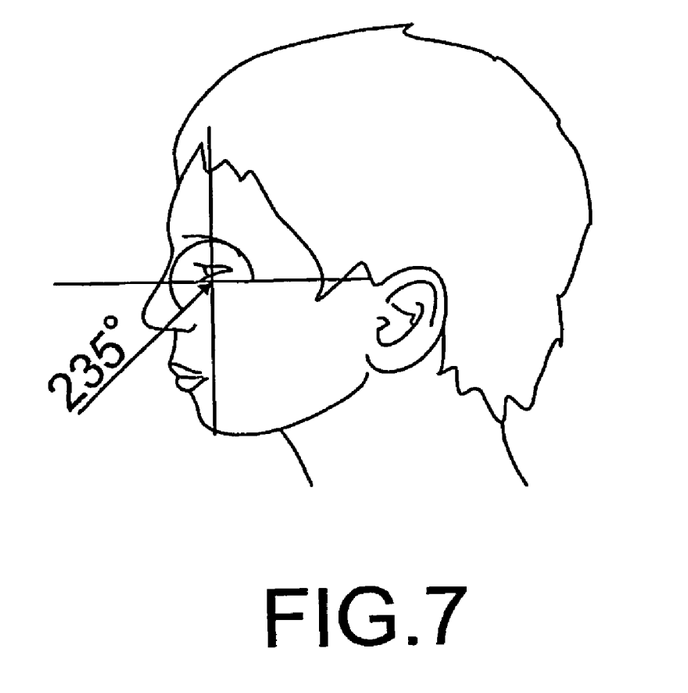
FIG. 7 Shows a side view of a patient's face, where it indicates the situation of the sagital plane, where the eye movement capturing means are positioned, seen from the right side FIG. 8 Shows an alternative embodiment of the invention, essentially applicable to children, which consists of incorporating a second smaller helmet, adapted to the size of the head, which can be attached to the helmet, which has the image recording means represented in FIG. 1, 3 or 5.

Both options of embodiment seen, with two video cameras (5) or just one camera (6) which records the reflections of a pair of mirrors (7) manage to record the images of all possible positions of either of the two eyes, seen from the angle of maximum induction, corresponding to the downward direction of the gaze and which, as has previously been explained, constitutes the angulation from which all eye movements can be viewed, without the eyelids getting in the way. Said angle of maximum induction covers the intersection of the coronal plane, in a position of 6 hours, the patient's face looking forward according to FIG. 6, plus the sagital plane at around 235°±5°, the eyes looking from the left profile as indicated in FIG. 7.

Optionally, the helmet (1) in any of its possible configurations incorporates in its front part a support for sight correcting lenses (9), which are integrated in the helmet (1) outside the focal path of the cameras (5, 6), so that the correcting lenses (9) do not get in the way when recording the eyes.

Figure 8:
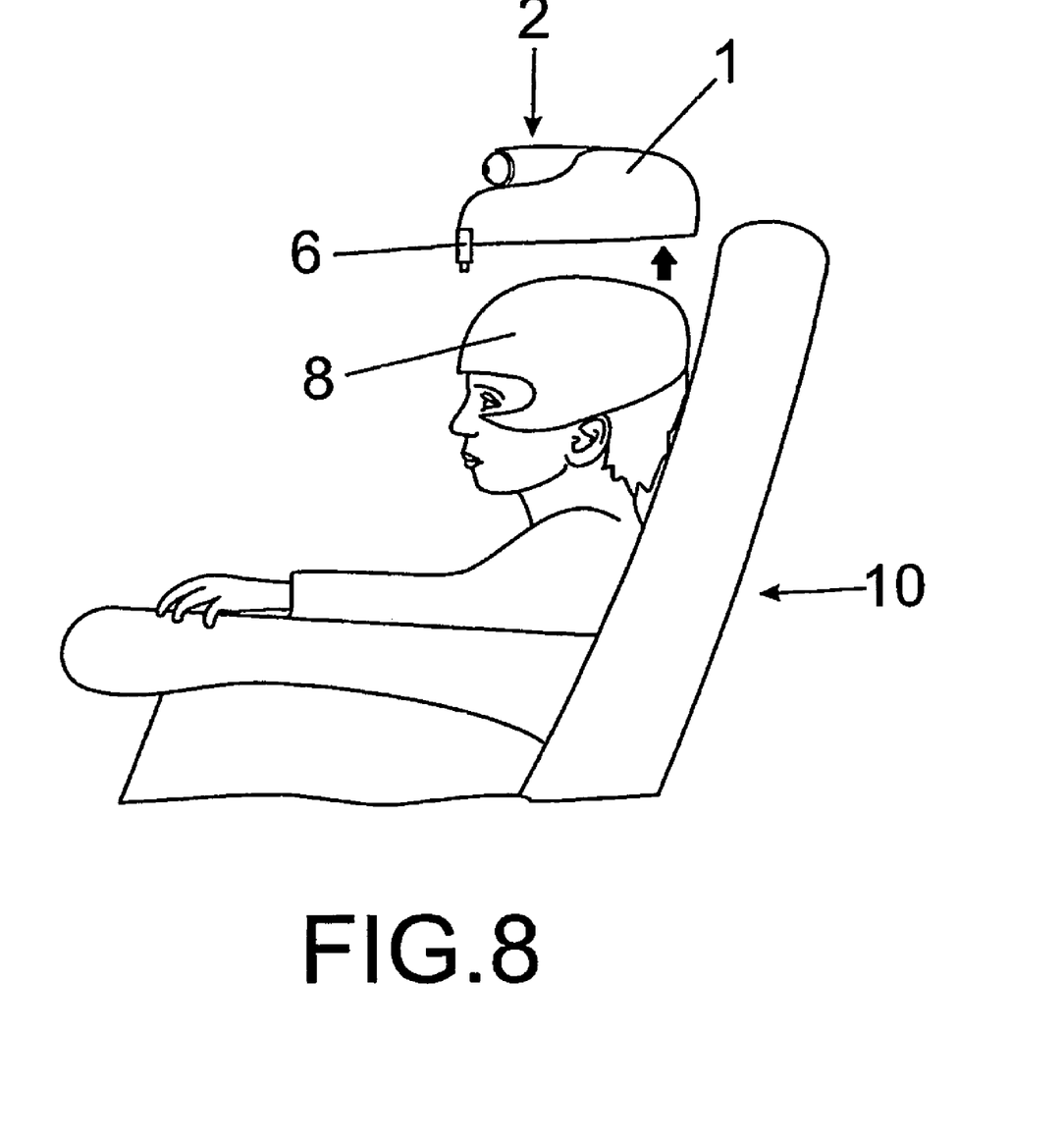

In order to anatomically adapt the helmet (1) to the patient's head size, it is planned to make 2 or 3 helmets of different size, taking into consideration the different ages and cranial perimeters. Furthermore, another helmet of less size between the previous and the head exercises the functions of adjustment of the size to perfection (8, 10). There should be several sizes of this second helmet which is interposed between the main one and the head.

The invention claimed is:

1. An eye movement sensor device for ophthalmologic examination of an eye movement anomaly in a patient, the sensor comprising:
   a helmet worn by the patient, the helmet comprising
      a head covering portion and
      a pair of cheek-extending portions defining a central open area for leaving eyes of the patient unobstructed by the helmet;
      wherein when the helmet is worn by the patient, each cheek-extending portion extends from proximal to an ear of the patient laterally over a cheek portion of the patient and has a distal end proximate to a respective front face portion under the respective eye of the patient;
   a light projector for projecting a light spot to be tracked by the patient, the projector disposed fixedly in an upper front portion of the helmet;
   a pair of mirrors, each mirror disposed on a respective cheek-extending portion; and
   an image recorder for recording a tracking eye movement of each eye of the patient;
   wherein each mirror is angled to reflect a respective image of the respective eye into the image recorder.

2. The sensor device of claim 1, wherein the helmet comprises a rear portion that is open to avoid dislocation of the helmet when the patient is in a sitting position.

3. The sensor device of claim 1, wherein the light projector comprises a first longitudinal centerline, each mirror comprising a second centerline, the first centerline being disposed in a first plane, the second centerlines being disposed in a second plane, the first plane bisecting the second plane.

4. The sensor device of claim 3, wherein the image recorder comprises a third centerline, the third centerline being disposed in the first plane.

5. The sensor device of claim 1, wherein the image recorder comprises a video camera.

6. The sensor device of claim 5, wherein the video camera comprises a weight in a range of 60-90 grams.

7. The sensor device of claim 5, wherein the video camera is a high resolution video camera comprising high color discrimination in light conditions required for ophthalmological examination.

8. The sensor device of claim 1, wherein the light projector comprises a laser.

9. The sensor device of claim 1, further comprising at least one support for supporting at least one sight correcting lens.

10. The sensor device of claim 1, wherein the central open area provides access to the eyes of the patient to an angle of maximum infraduction.

11. An eye movement sensor device for ophthalmologic examination of an eye movement anomaly in a patient, the sensor comprising:
   a helmet worn by the patient, the helmet comprising
      a head covering portion and
      a pair of cheek-extending portions defining a central open area for leaving eyes of the patient unobstructed by the helmet;
      wherein when the helmet is worn by the patient, each cheek-extending portion extends from proximal to an ear of the patient laterally over a cheek portion of the patient and has a distal end proximate to a respective front face portion under the respective eye of the patient;
   a light projector for projecting a light spot to be tracked by the patient, the projector disposed fixedly in an upper front portion of the helmet; and
   a pair of image recorders, each image recorder disposed on a respective cheek-extending portion and angled to record directly without intermediate reflection means a tracking eye movement of the respective eye of the patient.

12. The sensor device of claim 11, wherein the helmet comprises a rear portion that is open to avoid dislocation of the helmet when the patient is in a sitting position.

13. The sensor device of claim 11, wherein the light projector comprises a first longitudinal centerline, each image recorder comprising a second centerline, the first centerline being disposed in a first plane, the second centerlines being disposed in a second plane, the first plane bisecting the second plane.

14. The sensor device of claim 11, wherein at least one of the image recorders comprises a video camera.

15. The sensor device of claim 14, wherein the video camera is a high resolution video camera comprising high color discrimination in light conditions required for ophthalmological examination.

16. The sensor device of claim 11, further comprising at least one support for supporting at least one sight correcting lens.

17. The sensor device of claim 11, wherein the central open area provides access to the eyes of the patient to an angle of maximum infraduction.

18. A system for ophthalmologic examination of an eye movement anomaly in at least one patient, the system comprising:
   a projection screen;
   a first helmet worn by the patient, the first helmet comprising
      a head covering portion and
      a pair of cheek-extending portions defining a central open area for leaving eyes of the patient unobstructed by the helmet;
      wherein when the first helmet is worn by the patient, each cheek-extending portion extends from proximal to an ear of the patient laterally over a cheek portion of the patient and has a distal end proximate to a respective front face portion under the respective eye of the patient;
   a light projector for projecting a light spot to be tracked by the patient, the projector disposed fixedly in an upper front portion of the first helmet; and
   an image system, the image system comprising
      a pair of image recorders, each image recorder disposed on a respective cheek-extending portion and angled to record a tracking eye movement of the respective eye of the patient, or
      a pair of mirrors, each mirror disposed on a respective cheek-extending portion, an image recorder for recording the tracking eye movement of each eye of the patient; wherein each mirror is angled to reflect a respective image of the respective eye into the image recorder.

19. The system of claim 18, wherein the system further comprises a second helmet, the second helmet comprising a size suitable for a head size of a different patient than the at least one patient, the second helmet being configured substantially similar to the first helmet.

\* \* \* \* \*